United States Patent [19]

Haugwitz

[11] 4,288,368
[45] Sep. 8, 1981

[54] DITHIOACYLPROLINE DERIVATIVES

[75] Inventor: Rudiger D. Haugwitz, Titusville, N.J.

[73] Assignee: E. R. Squibb & Sons, Inc., Princeton, N.J.

[21] Appl. No.: 61,729

[22] Filed: Jul. 30, 1979

[51] Int. Cl.$^3$ ............... C07D 207/16; C07D 409/12
[52] U.S. Cl. ............ 260/326.35; 260/326.2; 260/326.25; 260/326.36; 260/326.45; 260/326.47; 544/333; 544/141; 544/327; 544/335; 544/140; 546/281; 546/238; 546/245; 546/279; 548/201; 548/236; 548/336; 548/374; 548/379; 424/274; 424/273 P; 424/267
[58] Field of Search ........... 260/326.2, 326.25, 326.35, 260/326.36, 326.45, 326.47; 544/141, 327, 335; 546/281; 548/201, 236, 336, 374

[56] References Cited

U.S. PATENT DOCUMENTS

| | | | |
|---|---|---|---|
| 4,105,776 | 8/1978 | Ondetti et al. | 424/274 |
| 4,211,786 | 7/1980 | Rovnyak | 548/379 |
| 4,241,076 | 12/1980 | Ondetti | 260/326.2 |

Primary Examiner—Henry R. Jiles
Assistant Examiner—Natalia Harkaway
Attorney, Agent, or Firm—Lawrence S. Levinson; Donald J. Barrack

[57] ABSTRACT

Compounds having the formula

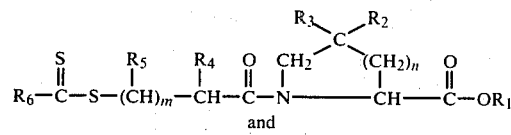

and

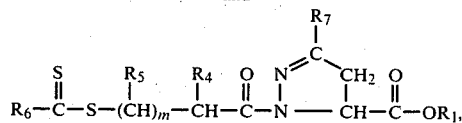

wherein:

$R_1$ is hydrogen, alkyl, aryl or arylalkyl;
$R_2$ is hydrogen and $R_3$ is hydrogen, hydroxy, alkoxy or halogen, or together $R_2$ and $R_3$ can be $=O$ or $-X-(CH_2)_t-X-$ wherein X is oxygen or sulfur and t is 2 or 3;
$R_4$ is hydrogen or alkyl;
$R_5$ is hydrogen, alkyl or trifluoromethyl;
$R_6$ is alkyl of 1 to 20 carbon atoms, aryl, arylalkyl or a 5- or 6-membered heterocyclic group having 1 or 2 nitrogen, sulfur or oxygen atoms in the ring;
$R_7$ is aryl;
m is 0, 1 or 2; and
n is 1 or 2 have useful hypotensive activity.

2 Claims, No Drawings

DITHIOACYLPROLINE DERIVATIVES

RELATED APPLICATIONS

United States patent application Ser. No. 018,548, filed Mar. 8, 1979, discloses mercaptoacyldihydropyrazole carboxylic acid derivatives having the formula

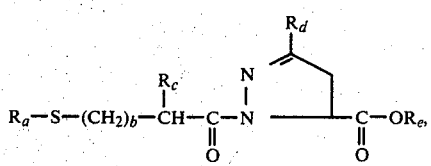

wherein $R_a$ is hydrogen, alkyl, aryl, arylalkyl,

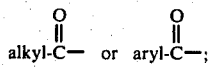

b is 0, 1 or 2; $R_c$ is hydrogen or alkyl; $R_d$ is aryl; and $R_e$ is hydrogen, alkyl or arylalkyl.

United States patent application Ser. No. 972,314, filed Dec. 22, 1978 discloses mercaptoacyl proline derivatives having the formula

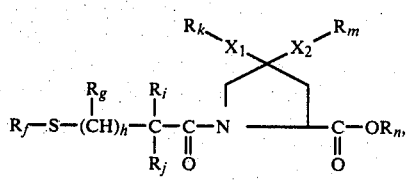

wherein, $R_f$ is hydrogen, acyl or

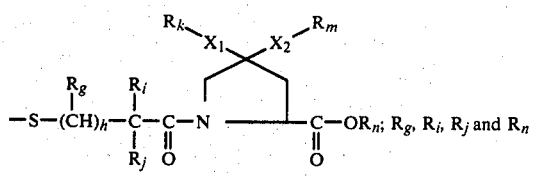

each is hydrogen or alkyl; $X_1$ and $X_2$ each is oxygen or sulfur; $R_k$ and $R_m$ each is alkyl or $R_k$ and $R_m$ join in a 2- or 3-carbon polymethylene chain to complete a 5- or 6-membered ring; and h is 0, 1 or 2.

United States patent application Ser. No. 52,691, filed July 2, 1979 discloses mercaptoacyl proline derivatives having the formula

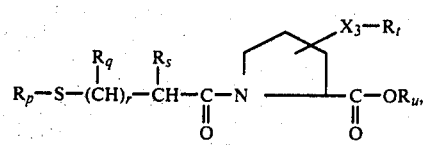

wherein $R_p$ is hydrogen, acyl, or

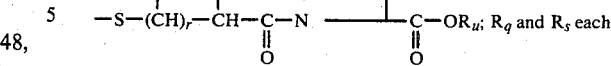

is hydrogen, alkyl or trifluoromethyl; r is 0, 1 or 2; $X_3$ is oxygen or sulfur; $R_t$ is alkyl, alkenyl, alkynyl, aryl or aryl-lower alkylene; and $R_u$ is hydrogen or alkyl.

United States patent application Ser. No. 37,255, filed May 9, 1979 discloses halogen substituted mercaptoacylprolines having the formula

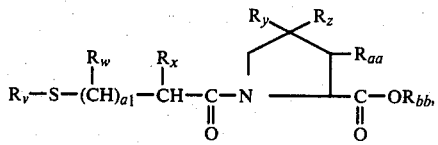

wherein $R_v$ is hydrogen, alkanoyl, phenylalkylenecarbonyl, or

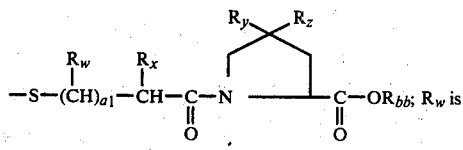

hydrogen, alkyl or trifluoromethyl; $R_x$ is hydrogen, alkyl, halogen or trifluoromethyl; $R_y$, $R_z$ and $R_{aa}$ each is hydrogen or halogen; $R_{bb}$ is hydrogen or alkyl; and $a_1$ is 0 or 1.

BACKGROUND OF THE INVENTION

United States Pat. No. 4,105,776, issued Aug. 8, 1978, describes a group of thioalkanoyl derivatives of azetidinepyrrolidine-, and piperidinecarboxylic acid compounds having the formula

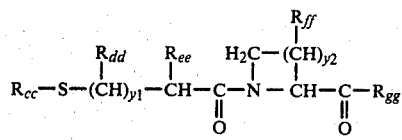

wherein $R_{cc}$ is hydrogen, alkyl, aryl, phenylalkyl, diphenylalkyl, triphenylalkyl, alkylthiomethyl, phenylalkylthiomethyl, alkanoylamidomethyl,

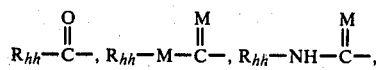

$R_{ii}$-S-, or $R_{jj}$; $R_{dd}$ and $R_{ee}$ each is hydrogen, phenyl, alkyl, or phenylalkyl; $R_{ff}$ is hydrogen, hydroxy or alkyl; $R_{gg}$ is hydroxy, —NH$_2$, or alkoxy; $y_1$ is 0, 1 or 2; $y_2$ is 1, 2, or 3; $R_{hh}$ is alkyl, phenyl or phenylalkyl; $R_{ii}$ is alkyl, aryl, hydroxyalkyl, or amino(carboxy)alkyl; $R_{jj}$ is

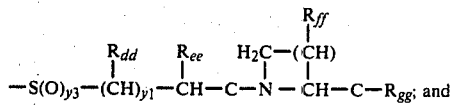

$y_3$ is 0, 1 or 2.

The compounds set forth above, under the headings "Related Applications" and "Background of the Invention" are disclosed as being useful as inhibitors of the conversion of the decapeptide angiotensin I to angiotensin II. They are, therefore, useful in reducing or relieving angiotensin related hypertension.

BRIEF DESCRIPTION OF THE INVENTION

Compounds having the formulas

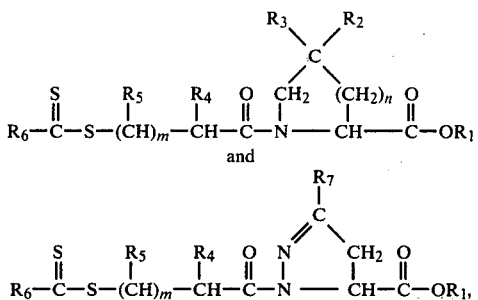

and basic salts thereof, have hypotensive activity. In formulas I and II, and throughout the specification, the symbols are as defined below.

$R_1$ is hydrogen, alkyl, aryl or arylalkyl;

$R_2$ is hydrogen and $R_3$ is hydrogen, hydroxy, alkoxy or halogen, or together $R_2$ and $R_3$ can be =O or, —X—$(CH_2)_t$—X— wherein X is oxygen or sulfur and t is 2 or 3;

$R_4$ is hydrogen or alkyl;

$R_5$ is hydrogen, alkyl or trifluoromethyl;

$R_6$ is alkyl of 1 to 20 carbon atoms, aryl, arylalkyl or a 5- or 6-membered heterocyclic group having 1 or 2 nitrogen, sulfur or oxygen atoms in the ring;

$R_7$ is aryl;

m is 0, 1 or 2; and n is 1 or 2.

The term "aryl", as used throughout the specification, either by itself or as part of a larger group, refers to phenyl or phenyl substituted with 1, 2 or 3 halogen, alkyl, alkoxy, sulfamyl, hydroxy,

alkyl-C—, nitro, amino, alkylamino, dialkylamino, trifluoromethyl, cyano or carboxyl groups. Phenyl is the preferred aryl group.

The terms "alkyl" and "alkoxy", as used throughout the specification (unless otherwise defined), either by themselves or as part of a larger group, refer to groups having 1 to 7 carbon atoms. Groups having 1, 2 or 3 carbon atoms are preferred.

The term "halogen", as used throughout the specification, either by itself or as part of a larger group, refers to fluorine, chlorine, bromine and iodine.

Exemplary of the heterocyclic "$R_6$ substituents" are thienyl, furyl, pyrrolyl, imidazolyl, oxazolyl, thiazolyl, pyrazolyl, pyridinyl, pyrimidinyl, morpholinyl and piperazinyl.

DETAILED DESCRIPTION OF THE INVENTION

The compounds of formulas I and II are useful as hypotensive agents. They inhibit the conversion of the decapeptide angiotensin I to angiotensin II and, therefore, are useful in reducing or relieving angiotensin related hypertension. The action of the enzyme renin on angiotensinogen, pseudoglobulin in blood plasma, produces angiotensin I. Angiotensin I is converted by angiotensin converting enzyme (ACE) to angiotensin II. The latter is an active pressor substance which has been implicated as the causative agent in various forms of hypertension in various mammalian species, e.g., rats and dogs. The compounds of this invention intervene in the angiotensinogen→(renin)→angiotensin I→(ACE)-→angiotensin II sequence by inhibiting angiotensin converting enzyme and reducing or eliminating the formation of the pressor substance angiotensin II. Thus by the administration of a composition containing one, or a combination of compounds, of formulas I and II angiotensin dependent hypertension in the species of mammal suffering therefrom is alleviated. A single dose, or preferably two to four divided daily doses, provided on a basis of about 0.1 to 100 mg. per kilogram of body weight per day, preferably about 1 to 15 mg. per kilogram of body weight per day is appropriate to reduce blood pressure. The substance is preferably administered orally, but parenteral routes such as the subcutaneous, intramuscular, intravenous or intraperitoneal routes can also be employed.

The compounds of this invention can also be formulated in combination with a diuretic for the treatment of hypertension. A combination product comprising a compound of this invention and a diuretic can be administered in an effective amount which comprises (for a 70 kg. mammal) a total daily dosage of about 30 to 600 mg., preferably about 30 to 300 mg., of a compound of this invention, and about 15 to 300 mg., preferably about 15 to 200 mg. of the diuretic, to a mammalian species in need thereof. Exemplary of the diuretics contemplated for use in combination with a compound of this invention are the thiazide diuretics, e.g., chlorthiazide, hydrochlorthiazide, flumethiazide, hydroglumethiazide, bendroflumethiazide, methychlothiazide, trichlormethiazide, polythiazide or benzthiazide, as well as ethacrynic acid, ticrynafen, chlorthalidone, furosemide, musolimine, bumetanide, triamterene, amiloride and spironolactone, and salts of such compounds.

The compounds of formula I and II can be formulated for use in the reduction of blood pressure in compositions such as tablets, capsules or elixirs for oral administration or in sterile solutions or suspensions for parenteral administration. About 10 to 500 mg. of a compound or mixture of compounds of formula I is compounded with a physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

The compounds of this invention can be obtained utilizing as a starting material the corresponding mercapto compound having the formula

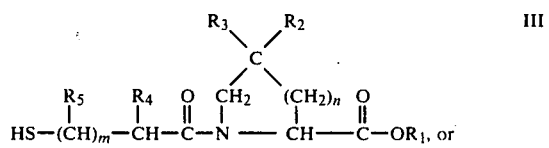

-continued

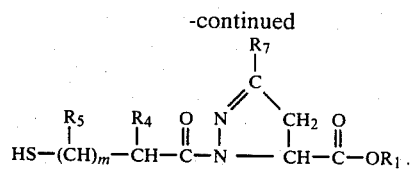  IV

The compounds of formulas III and IV, and methods for their preparation are disclosed in U.S. Pat. No. 4,105,776, issued Aug. 8, 1978, and U.S. Pat. No. 4,154,935, issued May 15, 1979, and in United States patent applications Ser. No. 972,314, filed Dec. 22, 1978; Ser. No. 018,548, filed Mar. 8, 1979; Ser. No 37,255, filed May 9, 1979; Ser. No. 52,691, filed July 2, 1979. The disclosures of the above references are incorporated herein by reference.

United States patent application Ser. No. 972,314, filed Dec. 22, 1978 discloses a method which can be used for the preparation of compounds of formula III wherein $R_2$ and $R_3$ are $-X-(CH_2)_r-X-$ and n is 1. As disclosed therein, the nitrogen atom of 4-hydroxyproline is first protected (e.g., with a carbobenzyloxy, p-toluenesulfonyl or acetyl group) and the hydroxy group is then oxidized to a keto group (e.g., in acetone with chromic acid in sulfuric acid). The keto group can be converted to the ketal or thioketal group by reacting the protected compound with the appropriate alcohol or thiol in the presence of an acid. Hydrogenolysis can be used to remove the nitrogen protecting group and the resulting compound can be coupled with the appropriate acyl halide.

United States patent application Ser. No. 52,691, filed July 2, 1979 discloses a method which can be used for the preparation of compounds of formula III wherein $R_2$ is hydrogen and $R_3$ is alkoxy and n is 1. As disclosed therein an ether proline derivative can be coupled with an acid or its chemical equivalent. The ether proline derivative can be prepared from a hydroxy proline. The hydroxy proline is acylated with an acylating agent such as acetic anhydride, acetyl chloride, propionic anhydride, butyric anhydride, benzylchloroformate, or the like, to protect the nitrogen. The hydroxy group can then be converted to an alkoxy group (the carboxyl group is also esterified) by reacting the N-protected compound with an alkyl halide (preferably an alkyl iodide) in the presence of silver oxide, sodium hydride, sodium hydroxide or the like. Alkaline hydrolysis of the resulting N-protected compound with a base such as barium hydroxide, sodium hydroxide, potassium hydroxide or the like yields the free acid (COOH) and then hydrolysis with a mineral acid, such as sulfuric acid, yields the ether proline derivative.

Reaction of a compound of formula III or IV with a nitrile having the formula $$R_6-C\equiv N \qquad V$$

yields the corresponding imino ether having the formula

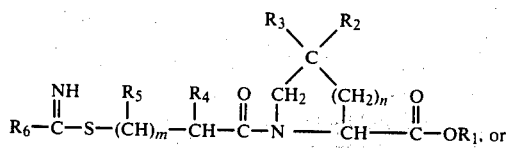 VI or

-continued

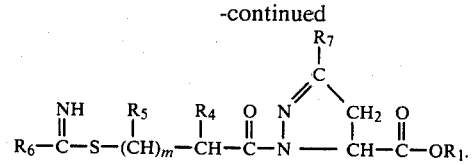 VII

The reaction can be run in an organic solvent, e.g., a halogenated hydrocarbon such as dichloromethane or chloroform, or ether. The reaction proceeds most readily in the presence of anhydrous hydrogen chloride.

Reaction of an imino ether of formula VI or VII with hydrogen sulfide in the presence of an organic base e.g., pyridine, yields the corresponding product of formula I or II. The reaction can be conveniently run by saturating a suspension (or solution) of a compound of formula VI or VII with hydrogen sulfide gas.

Alternatively, the products of this invention can be prepared by first reacting a nitrile of formula V with a mercapto carboxylic acid having the formula $$\underset{R_5}{\overset{\phantom{X}}{\text{HS}-(CH)_m-CH-C-OH}}\quad\underset{O}{\overset{R_4}{|}}\quad VIII$$

to yield a dithio ester having the formula $$\underset{R_6-C-S-(CH)_m-CH-C-OH}{\overset{S\phantom{XXX}R_5\phantom{XX}R_4\phantom{XX}O}{\| \phantom{XXXXXXX}|\phantom{XXXX}|\phantom{XXX}\|}}\quad IX$$

The reaction can be run following the procedure described above for the reaction of a compound of formulas III or IV with a compound of formula V.

The compound of formula IX can be coupled with an amino acid ester having the formula $$\begin{array}{c} R_3 \diagdown \phantom{X} \diagup R_2 \\ C \\ \diagup \phantom{X} \diagdown \\ CH_2 \phantom{XX} (CH_2)_n \phantom{XX} O \\ | \phantom{XXXXX} | \phantom{XXXX} \| \\ HN-\!\!-\!\!-CH-\!\!-\!\!-C-OR_1' \end{array} \qquad X$$

or $$\begin{array}{c} R_7 \\ | \\ C \\ \diagup \phantom{X} \diagdown \\ N \phantom{XXX} CH_2 \phantom{XX} O \\ | \phantom{XXXX} | \phantom{XXX} \| \\ HN-\!\!-\!\!-CH-C-OR_1' , \end{array} \qquad XI$$

wherein $R_1'$ is alkyl, aryl or arylalkyl, using known procedures to obtain the products of formula I and II. For example, a dithio ester of formula IX can be activated prior to its reaction with an ester of formula X or XI by formation of a mixed anhydride, symmetrical anhydride, acid chloride, active ester or the like. Those products of this invention wherein $R_1$ is hydrogen can be prepared by saponification of a corresponding ester. products of this invention comprises the alkylation of a dithioacid having the formula

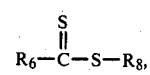 XII wherein $R_8$ is hydrogen or a cation such as ammonium or an alkali metal, with the appropriate halocarboxylic acid having the formula

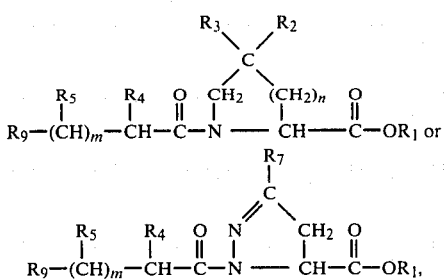

wherein $R_9$ is halogen or tosyl. The preparation of diothioacids of formula XII is described in Houben-Weyl, *Methoden der Organischen Chemie*, Vol. 9, Thieme Verlag, Stuttgart, 1955 and in Barton and Ellis, *Comprehensive Organic Chemistry*, Vol. 3, Pergamon Press, 1979.

Still another method for the preparation of the products of this invention comprises the thioacylation of a mercaptoamino acid of formula III or IV with a thioacid chloride having the formula

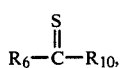 XV wherein $R_{10}$ is chlorine or bromine.

The compounds of this invention form salts with various inorganic and organic bases which are also within the scope of the invention. Such salts include ammonium salts, alkali metal salts like sodium and potassium salts (which are preferred), alkaline earth metal salts like the calcium and magnesium salts, salts with organic bases, e.g., dicyclohexylamine salt, benzathine, N-methyl-D-glucamine, hydrabamine salts, salts with amino acids like arginine, lysine and the like. The nontoxic, physiologically acceptable salts are preferred, although other salts are also useful, e.g., in isolating or purifying the product.

The compounds of formulas I and II each contains at least one asymmetric carbon and accordingly exist in stereoisomeric forms or in racemic mixtures thereof. The above described syntheses can utilize the racemate or one of the enantiomers as starting material. When the racemic starting material is used in the synthetic procedure, the stereoisomers obtained in the product can be separated by conventional fractional crystallization of the diastereomeric salt mixture formed, e.g., with an optically active amine. It is theorized that the activity of the racemic products is due mostly to the L-isomer with respect to the carbon of the amino acid, and this isomer is accordingly preferred.

The following examples are specific embodiments of this invention.

EXAMPLE 1

(S)-1-[2-Methyl-1-oxo-3-[(phenylthioxomethyl)thio]-propyl]-L-proline

A solution of 4.4 g (0.02 mole) of 1-(3-mercapto-2-methyl-1-oxopropyl)-L-proline and 5 g (~0.05 mole) of benzonitrile in 50 ml of methylene chloride is cooled to 0° C., saturated with hydrogen chloride and stirred for about 16 hours at room temperature. The solvent is removed in vacuo and the residue is triturated with petroleum ether; the solvent is decanted.

To the residue is added 50 ml of pyridine and the mixture is stirred vigorously and cooled to 0° C. Hydrogen sulfide is bubbled through the mixture for 3 hours. The mixture is poured into ice water, acidified with concentrated hydrochloric acid and extracted exhaustively with ethyl acetate. The organic layers are combined, dried (MgSO$_4$) and evaporated in vacuo to give a residue which is crystallized from ethyl acetate to give 2.1 g of the title compound, melting point 157°–158° C.

Analysis calc'd for $C_{16}H_{19}NO_3S_2$: C,56.95; H,5.68; N,4.15. Found: C,57.10; H,5.78 N,4.34.

EXAMPLE 2

(S)-1-[3-[[(4-Fluorophenyl)thioxomethyl]thio]-2-methyl-1-oxopropyl]-L-proline

A solution of 4.4 g (0.02 mole) of 1-(3-mercapto-2-methyl-1-oxopropyl)-L-proline and 5 g (~0.04 mole) of p-fluorobenzonitrile in 50 ml of methylene chloride is cooled to 0° C., saturated with hydrogen chloride and stirred for about 16 hours at room temperature. The solvent is removed in vacuo and the residue is triturated with petroleum ether; the solvent is decanted.

To the residue is added 50 ml of pyridine and the mixture is stirred vigorously and cooled to 0° C. Hydrogen sulfide is bubbled through the mixture for three hours. The mixture is poured into ice water, acidified with concentrated hydrochloric acid and extracted exhaustively with ethyl acetate. The organic layers are combined, dried, (MgSO$_4$) and evaporated in vacuo to give a residue which is crystallized from ethyl acetate to give 2.2 g of the title compound, melting point 114°–115° C.

Anal. Calc'd for $C_{16}H_{18}FNO_3S_2$: C,54.06; H,5.10 N,3.94. Found: C,54.22; H,5.26 N,3.98.

EXAMPLE 3

(S)-1-[2-Methyl-1-oxo-3-[(2-thienylthioxomethyl)thio]-propyl]-L-proline

A solution of 4.4 g (0.02 mole) of 1-(3-mercapto-2-methyl-1-oxopropyl)-L-proline and 5 g (0.05 mole) of 2-thiophenecarbonitrile in 50 ml of methylene chloride is cooled to 0° C., saturated with hydrogen chloride and stirred for about 16 hours at room temperature. The solvent is removed in vacuo and the residue is triturated with petroleum ether; the solvent is decanted.

To the residue is added 50 ml of pyridine and the mixture is stirred vigorously and cooled to 0° C. Hydrogen sulfide is bubbled through the mixture for 3 hours. The mixture is poured into ice water, acidified with concentrated hydrochloric acid and extracted exhaustively with ethyl acetate. The organic layers are combined, dried (MgSO$_4$) and evaporated in vacuo to give a residue which crystallizes from ethyl acetate to give 3.5 g of the title compound, melting point 149°–150° C.

Anal. Calc'd for $C_{14}H_{17}NO_3S_3$: C,48.95; H,4.99; N,4.08. Found: C,49.15; H,5.13; N,4.21.

EXAMPLE 4

(S)-1-[2-Methyl-1-oxo-3-[(1-thioxoethyl)thio]propyl]-L-proline

To a solution of 2.2 g of 1-(3-mercapto-2-methyl-1-oxopropyl)-L-proline, 5.1 ml of acetonitrile and 20 ml of methylene chloride is added 2 g of hydrogen chloride gas. The solution is allowed to stand for about 16 hours. The solvent is evaporated and the oily residue washed once with petroleum ether. The residue is treated with 50 ml of pyridine and hydrogen sulfide gas is introduced for three hours. The mixture is poured onto ice, made acidic with concentrated hydrochloric acid and extracted with ethyl acetate. The dried extract is evaporated to yield an oily residue which, on trituration with cold ether, solidifies, yielding 1.1 g of product. Recrystallization from acetonitrile yields the title compound, melting point 123°–125° C.

Anal. Cal'ds for $C_{11}H_{17}NO_3S_2$: C,47.97; H,6.22 N,5.09. Found: C,48.16; H,6.09; N,5.26.

EXAMPLE 5

(S)-1-[2-Methyl-1-oxo-3-[(1-thioxooctadecyl)-thio]-propyl]-L-proline

A solution of 2.2 g (0.01 mole) of 1-(3-mercapto-2-methyl-1-oxopropyl)-L-proline and 5.2 g. (0.02 mole) of stearonitrile in 70 ml of methylene chloride is cooled to 0° C., saturated with hydrogen chloride and stirred for about 16 hours at room temperature. The solvent is removed in vacuo and the residue is triturated with petroleum ether; the solvent is decanted.

To the residue is added 50 ml of pyridine and the mixture is stirred vigorously and cooled to 0° C. Hydrogen sulfide is bubbled through the mixture for 3 hours. The mixture is poured into ice water, acidified with concentrated hydrochloric acid and extracted exhaustively with ethyl acetate. The organic layers are combined, dried (MgSO$_4$) and evaporated in vacuo to give a residue which is crystallized from ether/petroleum ether to yield 1.7 g of the title compound, melting point 50°–51° C.

What is claimed is:

1. (S)-1-[2-Methyl-1-oxo-3-[(2-thienylthioxomethyl)-thio]propyl]-L-proline.

2. (S)-1-[2-Methyl-1-oxo-3-[(1-thioxooctadecyl)thio]-propyl]-L-proline.

* * * * *

UNITED STATES PATENT AND TRADEMARK OFFICE
CERTIFICATE OF CORRECTION

PATENT NO. : 4,288,368
DATED : September 8, 1981
INVENTOR(S) : Rudiger D. Haugwitz It is certified that error appears in the above-identified patent and that said Letters Patent are hereby corrected as shown below:

Col. 6, line 59, insert the following before "products", --Another method for the preparation of the--.

Signed and Sealed this

Tenth Day of November 1981

[SEAL]

Attest:

GERALD J. MOSSINGHOFF

Attesting Officer

Commissioner of Patents and Trademarks